United States Patent
Anderson et al.

(10) Patent No.: US 12,329,366 B2
(45) Date of Patent: Jun. 17, 2025

(54) MEDICAL PROCEDURE KIT AND A RELATED METHOD

(71) Applicant: Orthocell Limited, Murdoch (AU)

(72) Inventors: Paul Anderson, Murdoch (AU); Ming Hao Zheng, Murdoch (AU)

(73) Assignee: Orthocell Limited, Murdoch (AU)

( * ) Notice: Subject to any disclaimer, the term of this patent is extended or adjusted under 35 U.S.C. 154(b) by 625 days.

(21) Appl. No.: 16/613,758

(22) PCT Filed: Jun. 5, 2018

(86) PCT No.: PCT/AU2018/050558
§ 371 (c)(1),
(2) Date: Nov. 14, 2019

(87) PCT Pub. No.: WO2018/223183
PCT Pub. Date: Dec. 13, 2018

(65) Prior Publication Data
US 2020/0100775 A1    Apr. 2, 2020

(30) Foreign Application Priority Data
Jun. 5, 2017    (JP) .................... 2017-110996

(51) Int. Cl.
*A61B 10/02* (2006.01)
*A61L 27/24* (2006.01)
*A61L 27/36* (2006.01)

(52) U.S. Cl.
CPC .......... *A61B 10/025* (2013.01); *A61L 27/24* (2013.01); *A61L 27/3608* (2013.01); *A61B 2010/0258* (2013.01)

(58) Field of Classification Search
CPC ...... A61K 35/00; A61L 27/3604; A61M 1/79; A61B 50/30
See application file for complete search history.

(56) References Cited

U.S. PATENT DOCUMENTS

| | | | |
|---|---|---|---|
| 6,299,763 B1 | 10/2001 | Ashman | |
| 2002/0161449 A1 | 10/2002 | Muschler | |
| 2008/0243028 A1* | 10/2008 | Howard | A61M 1/79 |
| | | | 600/565 |
| 2009/0099548 A1* | 4/2009 | Son | A61K 35/35 |
| | | | 604/522 |
| 2011/0262405 A1 | 10/2011 | Segina et al. | |
| 2012/0301507 A1 | 11/2012 | Zheng | |
| 2014/0276384 A1* | 9/2014 | Schwab | A61M 3/005 |
| | | | 604/82 |
| 2020/0121463 A1 | 4/2020 | Yoshikawa et al. | |

FOREIGN PATENT DOCUMENTS

| | | | | |
|---|---|---|---|---|
| EP | 1731113 | | 12/2006 | |
| JP | 2016/013094 | | 1/2016 | |
| WO | 1995/24469 | | 9/1995 | |
| WO | 2008/050922 | | 5/2008 | |
| WO | 2008/109807 | | 9/2008 | |
| WO | 2010/108237 | | 9/2010 | |
| WO | WO-2013179913 A1 * | 12/2013 | | C12M 21/08 |
| WO | 2016098108 | | 6/2016 | |

OTHER PUBLICATIONS

Steinwachs et al (Athrosc Tech, 2014, vol. 3, pp. e279-e282) (Year: 2014).*
Liu et al (Bio Protoc, Oct. 20, 2015, vol. 5, pp. 1-14) (Year: 2015).*
WO-2013179913-A1 (Google English Translation, downloaded Nov. 2023) (Year: 2023).*
Parenteau-Bareil, Remi, et al., (2010) "Collagen-Based Biomaterials for Tissue Engineering Applications", Materials, 3:1863-1887.
Nixon, A.J., et al., (2015) "A chondrocyte infiltrated collagen type I/III membrane (MACI® implant) improves cartilage healing in the equine patellofemoral joint model", Osteoarthritis and Cartilage, 23:648-660.
Marlovits, Stefan, et al., (2006) "Cartilage repair. Generations of autologous chondrocyte transplantation", European Journal of Radiology, Elsevier Science, NL, 57(1):24-31.
Gibson et al., (2006) "Matrix-Induced Autologous Chondrocyte Implantation", New Techniques in Cartilage Surgery, 262-265.

* cited by examiner

*Primary Examiner* — Mark V Stevens
(74) *Attorney, Agent, or Firm* — Todd Esker; Bozicevic, Field & Francis LLP (57) ABSTRACT

The present disclosure provides a medical procedure kit for ameliorating tissue damage in a patient, the kit comprising a container enclosing a receptacle, an extractor for extracting biological material including autologous cells from the patient, a strainer for straining autologous cells from the biological material and an implantable support having a surface onto which the autologous cells can adhere, the implantable support configured to be received by the receptacle. Also disclosed are related methods of manufacturing a medical material and using the medical procedure kit.

13 Claims, 5 Drawing Sheets

MEDICAL PROCEDURE KIT AND A RELATED METHOD

TECHNICAL FIELD

The present disclosure relates to a medical procedure kit and a related method of preparing an implantable support for ameliorating tissue damage using the medical procedure kit.

BACKGROUND

A known technique for facilitating the repair of tissue damage in a patient involves introducing cells, such as autologous cells including stem cells, to the site of the tissue damage to increase the rate of tissue regeneration. The cells may be obtained from autologous tissue isolated from the patient, such as cartilage. The autologous tissue is then typically treated to isolate the cells, for example, according to a procedure described in PCT/AU2010/000360 and "Regulative Mechanisms of Chondrocyte Adhesion" (Schmal et al. 2006, Tissue Engineering, Volume 12, Number 4, pp. 741-750). In this regard, tissue such as cartilage requires mechanical disruption and/or digestion in order to weaken the interaction between the cells. The cells are then typically separated from a remainder of the tissue, washed, cultured for several days to increase cell count, and deposited on an implantable support or scaffold for a suitable period of time to allow for cell growth on and adherence to the scaffold. The cell-scaffold composition may then be implanted at the site of the tissue damage. The period of time that the cells are allowed to grow on the scaffold may vary. For example, PCT/AU2010/000360 describes known techniques where cells are cultured for 4 to 10 days on a scaffold, and further discloses a method where less than 2 hours after the cells have been applied to the scaffold, the cell-scaffold composition can be implanted at the site of tissue damage.

It is to be understood that the any description above of known methods, techniques or devices does not constitute an admission that the description forms a part of the common general knowledge in the art in any country.

SUMMARY

In broad terms, at least one embodiment of the disclosed kit or method may be applicable to a way of ameliorating tissue damage, which involves obtaining cells from autologous biological material that does not require treatment for several days, in order to weaken the interaction between the cells for example, prior to deposition on an implantable support. Such biological material, for example bone marrow, may have a consistency that does not require mechanical disruption (for example, using blenders, sieves, homogenizers, pressure cells, and the like) and/or digestion to weaken the interaction between the cells.

According to a first aspect, there is provided a medical procedure kit for ameliorating tissue damage in a patient, the kit comprising a container enclosing the following components:
- a receptacle;
- an extractor for extracting biological material including autologous cells from the patient;
- a strainer for straining the autologous cells from the biological material; and
- an implantable support having a surface onto which the autologous cells can adhere, the implantable support configured to be received by the receptacle.

The biological material may be of the type that can be aspirated from a patient (such as but not limited to bone marrow) using the extractor in the form of a needle. The biological material may be of the type that does not have a particular kind of organised structure (such as cartilage), so as to require mechanical disruption as described above. The biological material may be material that has an in vivo fluid or gelatinous state.

Thus, once the biological material has been extracted, the autologous cells can be separated from the biological material using the strainer and immediately applied to the implantable support. After a relatively short period of time, for example less than 2 hours, or between about 5 mins and 1 hour 50 mins, or between about 10 mins and 1 hour 40 mins, or between about 15 mins and 1.5 hours, the implantable support now loaded with autologous cells can be implanted at the site of the tissue damage. The kit may therefore facilitate the extraction of biological material, and the implantation into the patient of the support loaded with cells from the biological material, in a single surgery. Further, by providing a kit comprising a container with the components above, the kit may be brought into an operating theatre with all the components necessary for the amelioration of particular tissue damage.

The container may be opened to access the components therein. Prior to opening the container a first time for use, the container may be sealed closed, preferably hermetically sealed. An internal region of the kit and the components may be sterilised prior to opening the container the first time.

In this manner, the kit may be brought into the operating theatre while the container is sealed closed, only to be opened immediately prior to use, thus potentially providing the advantage of sterilised, ready-to-use implements for a medical procedure.

The container may comprise predefined storage locations for one or more of the implantable support, extractor and strainer.

The receptacle may be integrated with the container. The receptacle may be a depression formed in a surface in an inner region of the container.

The extractor may comprise a hollow needle and a syringe. The hollow needle and syringe may be provided as separate components in the container and may be demountably attachable to each other. The extractor may further comprise a conduit demountably attachable at one end to the hollow needle and at an opposite end to the syringe. The hollow needle may be a puncture needle capable of extracting or aspirating bone marrow from a patient.

The implantable support may be a collagen membrane.

The biological material may exclude biological material considered to be tissue in this specification.

According to a second aspect, there is provided a method of manufacturing an implantable medical material suitable for at least assisting in ameliorating tissue damage in a mammalian body, the method comprising:
- opening the kit in accordance with the first aspect;
- placing the implantable support in the receptacle;
- covering the receptacle with the strainer;
- depositing biological material collected from the mammalian body on the strainer and allowing autologous cells from the biological material to pass through the strainer onto the implantable support;
- holding the implantable support and autologous cells in the receptacle for a period of time to transform the implantable support into the implantable medical material; and removing the implantable medical material from the receptacle.

According to a third aspect, there is provided a method of using the kit according to the first aspect, the method comprising:
opening the kit;
placing the implantable support in the receptacle;
covering the receptacle with the strainer;
depositing biological material collected from a mammalian body on the strainer and allowing autologous cells from the biological material to pass through the strainer onto the implantable support;
holding the implantable support and autologous cells in the receptacle for a period of time; and
removing the implantable support from the receptacle.

According to one or more embodiments of the second and third aspects, the period of time may be less than 2 hours, or approximately between 15 minutes and 2 hours, or between about 5 mins and 1 hour 50 mins, or between about 10 mins and 1 hour 40 mins, or between about 15 mins and 1.5 hours.

The biological material may be of a type that: (a) does not have a particular kind of organised structure; or (b) has an in-vivo fluid or gelatinous state.

The method according to the second or third aspects may further comprise using the extractor to extract the biological material from the mammalian body prior to depositing the biological material.

BRIEF DESCRIPTION OF DRAWINGS

Notwithstanding any other forms which may fall within the scope of the present disclosure as set forth in the Summary, specific embodiments will now be described, by way of example only, with reference to the accompanying drawings in which:

FIG. 4b shows a sectional view of a strainer incorporated in the kit when placed above the receptacle shown in FIG. 4a.

DETAILED DESCRIPTION

Throughout this specification, unless the context otherwise provides, the term "tissue" refers to an aggregate of cells that forms an organised kind of structure and carries out a particular function. For the avoidance of doubt, autologous biological material such as cartilage, which requires mechanical disruption and/or digestion to break down the cartilage structure and isolate cells therefrom, is considered to be a "tissue". In contrast, biological material such as bone marrow, which can be aspirated from a patient and which does not have a particular kind of organised structure, is not considered to be a "tissue".

Figure 1:
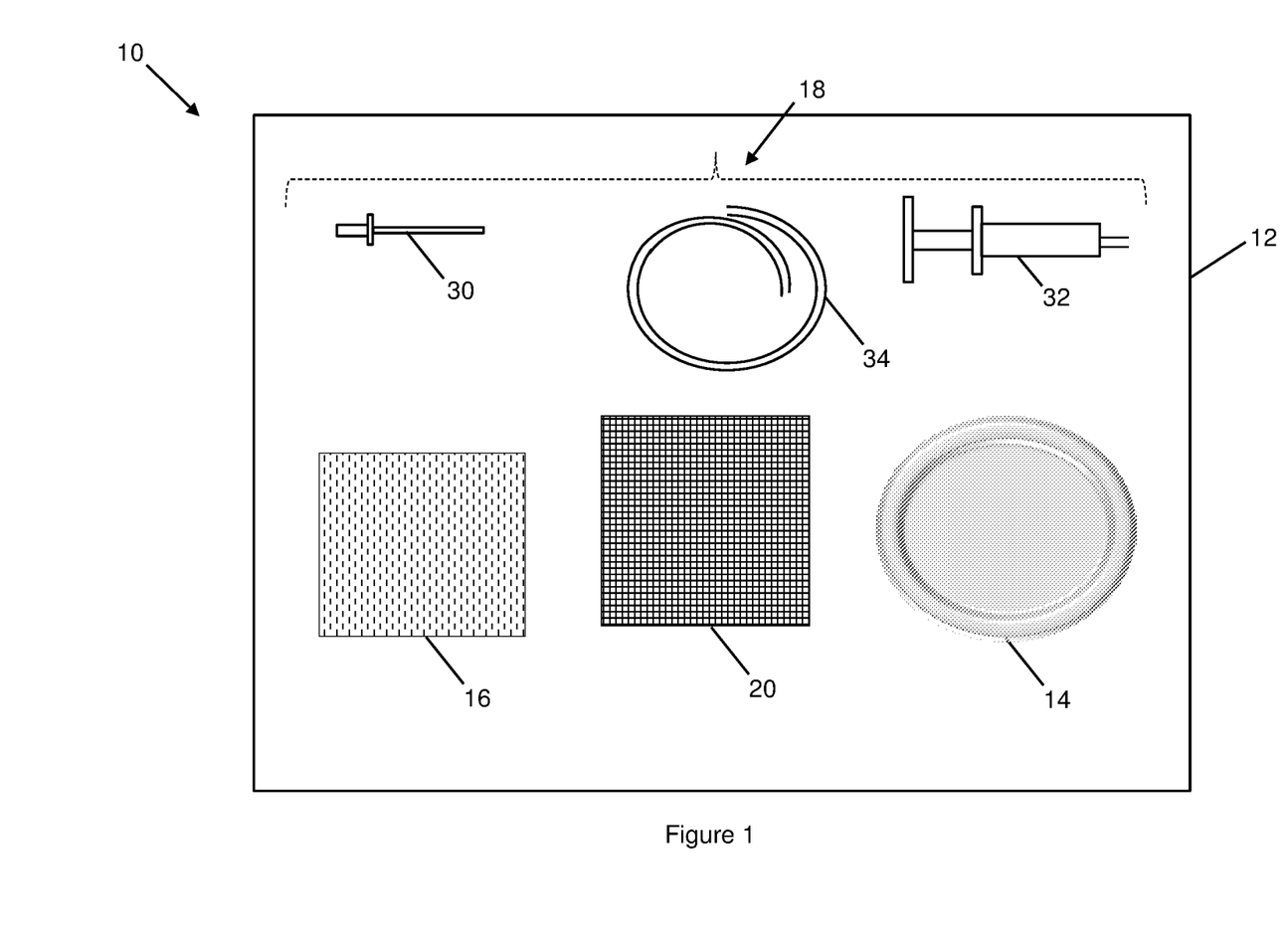
FIG. 1 shows a plan view of an embodiment of the disclosed kit.
Figure 2:
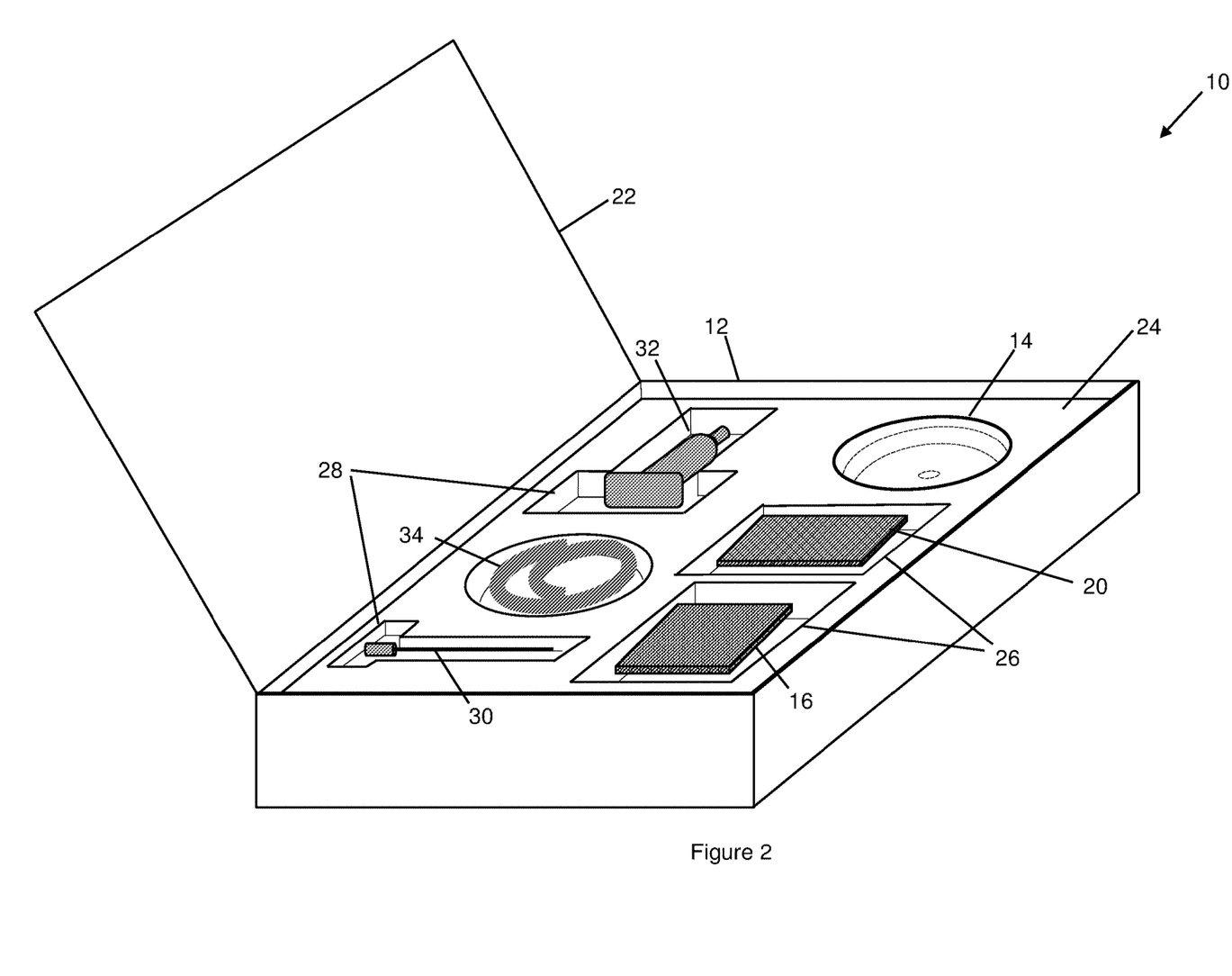
FIG. 2 shows a perspective view of an embodiment of the kit.

FIGS. 1 and 2 show a medical procedure kit 10 for ameliorating tissue damage in a patient. The kit 10 comprises a container 12 enclosing a plurality of components including a receptacle 14, an implantable support 16, an extractor 18 and a strainer 20. The extractor 18 is capable of extracting biological material including autologous cells from the patient. The cell strainer 20 is arranged to strain autologous cells from the biological material. The implantable support 16 has a surface onto which the autologous cells, strained from the biological material, can adhere. The implantable support is also configured to be received by and at least partially line the receptacle 14.

To provide context, in general terms the kit 10 may be used according to the following brief example. First, the implantable support 16 may be placed in the receptacle 14 and biological material including autologous cells may be extracted from the patient using the extractor 18. The strainer 20 can then be placed above the receptacle 14 (and the implantable support 16 in the receptacle 14), and the extracted material can be deposited by the extractor 18 onto the strainer 20 for at least some of the autologous cells, which may include stem cells, to pass through the strainer 20 and onto the support 16 in the receptacle 14.

Figure 4A:
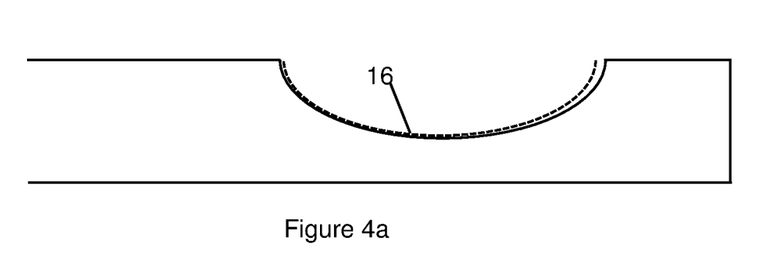
FIG. 4a shows a sectional view of an implantable support incorporated in the kit placed in a receptacle provided in a support of the kit.
Figure 4B:
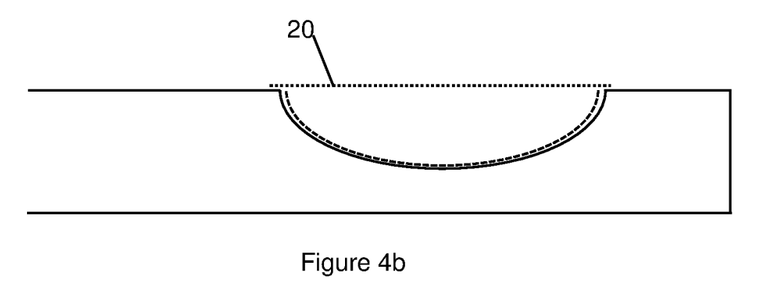
Figure 4C:
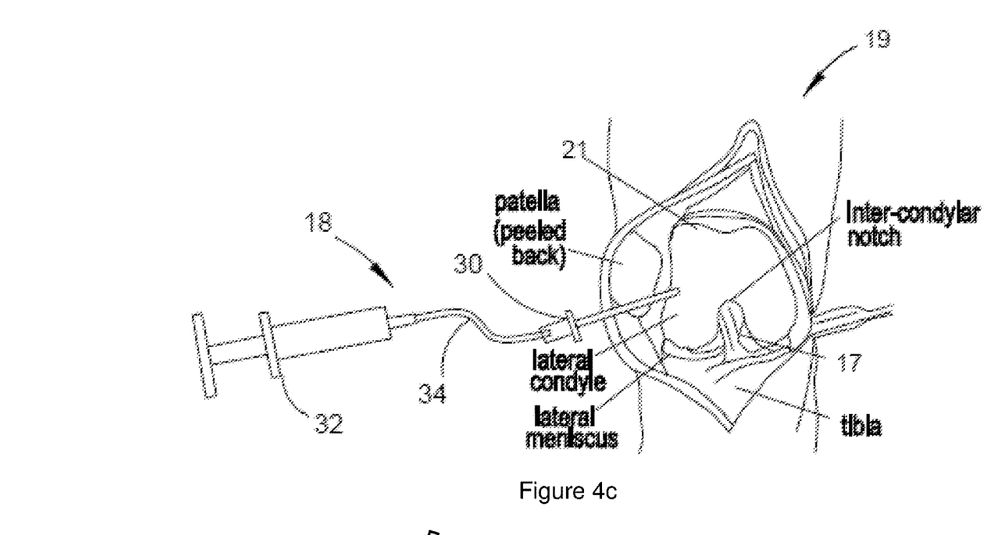
FIG. 4c shows a front view of an extractor incorporated in the kit, in use in accordance with the disclosed method.

According to a specific embodiment, which will be described below, the kit 10 may be particularly suitable for repairing or ameliorating a torn anterior cruciate ligament (ACL) 17 in a patient's knee 19 (see FIG. 4c). FIG. 2 in particular shows an open container 12 according to this embodiment. Prior to use, the container 12 encloses its contents so that the contents are isolated from an external environment. The container 12 in this embodiment comprises a box-like structure including a lid or cover 22 that can be moved to open the container 12 to access its contents. In this embodiment, the cover 22 remains connected (e.g. hinged) to a remainder of the container 12 after opening. However, it will be appreciated that in other embodiments the cover 12 may be completely removed from a remainder of the container 12.

Preferably, an internal region of the container 12 and the components therein are sterilised. The internal region and components are preferably sterilised prior to closing the container 12 (e.g. when assembling and packaging the kit 10). For example, the internal region and components may be sterilised using a gamma ray steriliser. It is also preferable that once the kit 10 is assembled and sterilised, the container 12 is hermetically sealed closed, to be opened only immediately prior to use. In this manner, the kit 10 may be brought into, for example, an operating theatre while the container 12 is sealed closed, only to be opened immediately prior to use. Thus, the kit 10 may provide sterilised, ready-to-use implements for a medical procedure. It will be appreciated that in other embodiments, the internal region and components may be sterilised after opening the container 12 instead of or in addition to sterilisation prior to sealing the container 12.

According to a specific embodiment, an internal region of the container 12 comprises a surface 24 configured with predefined storage locations for receiving particular components of the kit 10. The predefined storage locations may for example be holes (e.g. for holding removable receptacles), indents and/or depressions. In another example, indents and/or depressions may be configured with a shape corresponding to the specific component of the kit 10 to facilitate the holding of components in place. For example, rectangular or circular depressions may be provided for each of the implantable support 16 and the strainer 20, and a generally longitudinal T-shaped depression may be provided for the extractor 18 (or components thereof as described below).

The receptacle 14 in this embodiment is also provided in the form of a depression or well in the surface 24.

The implantable support in this embodiment is a sheet-like collagen membrane 16. The membrane 16 may be a rectangular sheet. For example, the membrane 16 may have a length of between 2 cm and 5 cm, and a width of between 2 cm and 5 cm. In a specific example, the membrane 16 may have a length and width of 3 cm and 4 cm, respectively. Examples of presently commercially available collagen membranes that may be used include CelGro® scaffold or Bio-Tide® collagen membrane. However, it will be appreciated that any suitable implantable support for use in cell implantation may be used. As mentioned above, the membrane 16 is also configured to be received by the receptacle 14. For example, the membrane 16 preferably has dimensions that allow it to line a bottom of the receptacle 14 such that an exposed surface of the membrane 16 faces upwards to receive cells.

The extractor 18 according to this embodiment comprises a plurality of components including a hollow needle 30, a syringe 32 and a conduit or tubing 34. Prior to use, in this embodiment the needle 30, syringe 32 and tubing 34 are provided in the kit 10 as separate components that are demountably attachable to one another. More specifically, the needle 30 is attachable to one end of the tubing 34 and the syringe 32 is attachable to an opposite end of the tubing 34. Continuing with the example of repairing or ameliorating a torn ACL, according to a specific embodiment the extractor 18 is particularly suitable for aspiration of bone marrow from a patient (for example, a femur). Thus, the needle 30 may be a puncture needle or bone marrow aspiration needle.

It will be appreciated that although the tubing 34 may provide advantages such as ease of manoeuvrability when extracting biological material from a patient, in other applications the tubing 34 may not be required. Thus, other embodiments of the kit 10 may not include the tubing 34.

The strainer 20 may be used to obtain a substantially uniform distribution of cells on the membrane 16. The strainer 20 may also serve to filter out undesirable biological material (such as fatty matter in the case of bone marrow) from being deposited onto the membrane 16. The strainer 20 may be provided in any suitable form, such as a sheet of mesh or a cup-like receptacle comprising mesh bottom and side walls. The strainer 20 may for example have a mesh size of up to 2 mm, or between about 20 µm to 2 mm, such as but not limited to about 40 µm, or 70 µm, or 100 µm, or 1 mm, or 1.5 mm. A person skilled in the art will appreciate that the size of the mesh of the strainer 20 may vary across different embodiments of the kit 10 depending on the particular application.

It will be appreciated that embodiments of the disclosed kit may offer the advantage of being brought into an operating theatre with all the components necessary for the repair or amelioration of particular tissue damage (such as a torn ACL) in a patient. Additionally, in preferable embodiments, components of the kit 10 as well as an internal region of the container 12 are pre-sterilised so that the kit 10 is ready to be used as soon as the container 12 is opened, thus potentially adding to the convenience and reducing preparation time.

Figure 3:
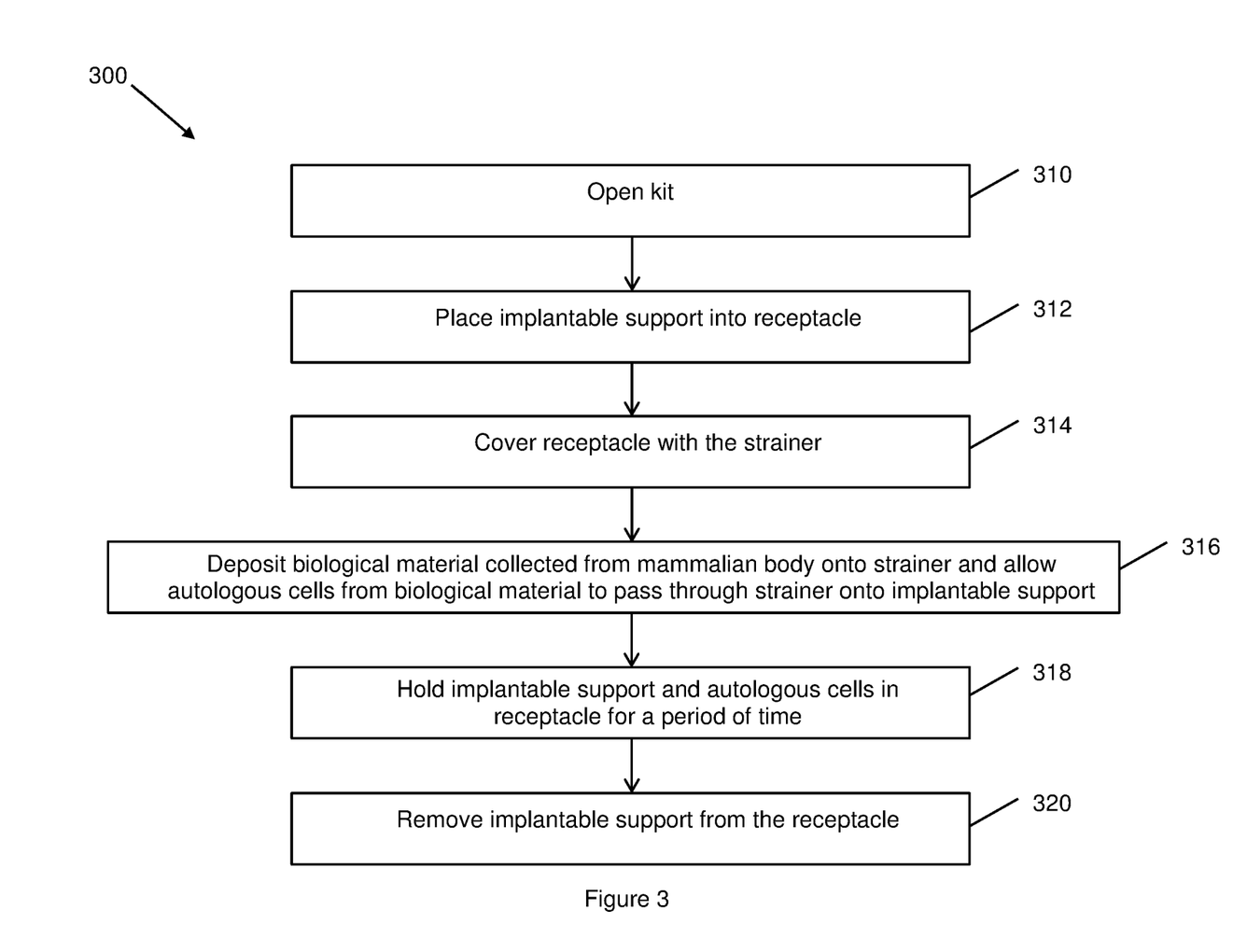
FIG. 3 shows a flow chart for an embodiment of the disclosed method.

FIG. 3 shows a flow chart of the method 300 according to another aspect of the present disclosure. The method 300 according to an embodiment comprises a first step 310 of opening the kit 10. The method 300 then comprises the step 312 of placing the implantable support 16 in the receptacle 14, an example of which is shown in FIG. 4a. In this example, the implantable support 16 is implemented as a sheet-like cell membrane, and thus in other words step 312 may involve at least partially lining the receptacle 14 with the membrane 16.

At step 314 the receptacle 14 is covered with the strainer 20. If the strainer 20 has suitable dimensions, step 314 may involve resting the strainer 20 on a rim surrounding an opening of the receptacle 14, as shown in FIG. 4b. Alternatively, a user may hold the strainer 20 above the receptacle 14.

Before the next step 316, biological material is extracted from a mammalian body, such as from the body of the patient. As described above, the biological material may be bone marrow extracted using the extractor 18, which according to an embodiment, comprises a hollow aspiration needle 30, a syringe 32 and tubing 26. Continuing with the example of facilitating the repair of a torn ACL, the bone marrow may be aspirated from a patient's femur 21 in the vicinity of the torn ACL 17, for example, as shown in FIG. 4c. More specifically, the needle 30 may be punched into the femur 21, and a plunger of the syringe 32 may then be drawn or pulled, to aspirate the bone marrow.

Figure 4D:
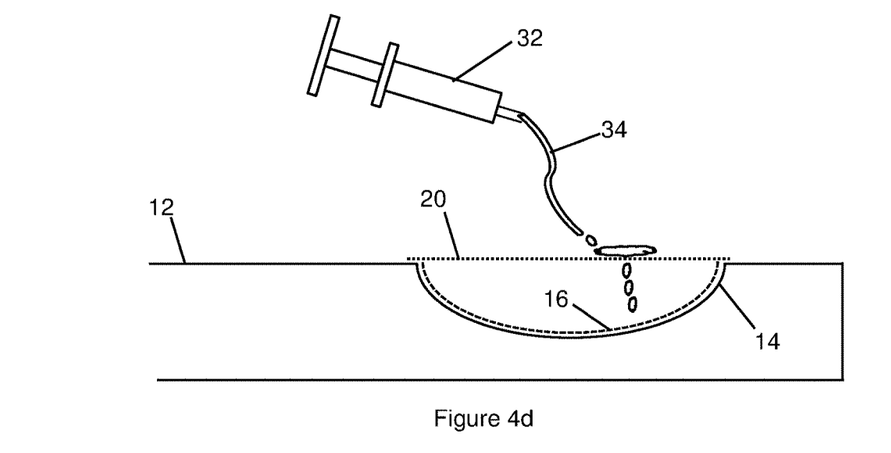
FIG. 4d shows a sectional view of the extractor depositing biological material through the strainer into the receptacle.

At step 316 the biological material removed from the patient is deposited on the strainer 20. This may be achieved in this embodiment by pushing the plunger of the syringe 32. Autologous cells from the biological material pass through the strainer 20 onto the implantable support. An example of step 316 is shown in FIG. 4d. In a specific non-limiting example, approximately 2 mL of cellular material may be strained into the receptacle 14. Additionally, the method 300 may include spreading the cells deposited on the membrane 16 using a spreader. The method 300 may also include applying cell culture medium into the receptacle 14 to keep the membrane 16 and cells moist. Accordingly, in further embodiments a spreading implement and/or vessel containing cell culture medium may also be included in the kit 10.

Step 318 involves holding the implantable support 16 and cells in the receptacle 14 for a period of time. The period of time is sufficient to allow the autologous cells from the biological material, which may include stem cells, to adhere and/or grow on the implantable support 16. The period of time may be less than 2 hours. According to an embodiment, the period of time is between approximately 15 minutes and 2 hours. Alternatively, the period of time may be between about 5 mins and 1 hour 50 mins, or between about 10 mins and 1 hour 40 mins, or between about 15 mins and 1.5 hours. During the period of time, the cells may be held on the support 16 in the receptacle 14 at a surrounding temperature of approximately the average human core body temperature, such as around 37° Celsius. After step 318, the implantable support 16 has now been transformed into an implantable medical material suitable for at least assisting in ameliorating tissue damage.

Finally, at step 320 the method 300 comprises removing the implantable support 16 from the receptacle 14 after being held in the receptacle 14 for the period of time. The implantable support 16 is now loaded with cells and ready to be applied to the site of the tissue damage to facilitate repair and increase the rate of tissue regeneration. For example, the support 16 may be applied around a torn ACL.

Known techniques for facilitating the repair of tissue damage in a patient often involve treating biological tissue and culturing the cells isolated from the tissue prior to deposition on an implantable support, a process which may take several days or weeks. These known techniques may also involve culturing the cells further on the support for several more days. In contrast, embodiments of the kit 10 may be particularly useful when the source of the cells, i.e. the extracted biological material, does not require several days of treatment in order to isolate the cells. Embodiments of the kit 10 may also be particularly useful for preparing cell membranes, such as CelGro® scaffold, on which cells can be directly deposited and held for a relatively short time (e.g. 15 minutes to 2 hours) prior to application at the site of tissue damage. The kit 10 may thus provide all items necessary for preparing these cell membranes up until a time they are ready to be inserted into a patient, including tools for extracting the cells as well as tools for depositing and holding the cells on the membrane.

Whilst a specific embodiment of the kit and method has been described, it should be appreciated that the kit and method may be embodied in many other forms. It will be understood to persons skilled in the art that many modifications may be made without departing from the spirit and scope of the disclosure.

For example, the implantable support according to other embodiments may also have a different shape and configuration, such as a circular or "butterfly-shaped" patch instead of a rectangular shape.

As another example, instead of depressions/indents as the predetermined storage locations of the container 12, a container according to another embodiment may comprise dividers separating the internal region of the container 12 into box-like compartments for each component of the kit.

In yet another example, instead of the lid 22 shown in FIG. 2, the container 12 may comprise a plastic cover wrapped over and/or around the box-like structure, such as a shrink-wrapped plastic cover.

As another example, in addition to or instead of the box-like structure and lid 22 shown in FIG. 2, the container may comprise a sealable bag, for example, made of plastics material.

As another example, instead of providing one of each component, the container of the kit may enclose multiples of one or more of the components. For example, the kit may comprise two or more strainers having the same or different mesh sizes (for example, to suit different application) and/or two or more implantable supports. Thus, if a strainer or implantable support is accidentally dropped, damaged or rendered unusable, an extra strainer or implantable support is provided.

In the claims which follow and in the preceding description of the disclosed kit and method, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the kit and method as disclosed herein.

It is to be understood that, if any prior art publication is referred to herein, such reference does not constitute an admission that the publication forms a part of the common general knowledge in the art, in Australia or any other country.

The invention claimed is:

1. A medical procedure kit for ameliorating tissue damage in a patient, the kit comprising a container enclosing the following components:
   a receptacle integrally formed as part of the container;
   a hollow needle for extracting bone marrow which contains cells from the patient;
   a cell strainer comprising a mesh filter dimensioned to allow cells from the bone marrow to pass through and filter out undesirable biological matter from passing through the mesh filter to produce isolated cells, the cell strainer having a dimension larger than the receptacle such that the cell strainer is positionable over the receptacle;
   an implantable collagen membrane having a dimension smaller than the receptacle such that the implantable collagen membrane is receivable in the receptacle, the implantable collagen membrane having a surface onto which the isolated cells can adhere; and
   predefined storage locations dimensioned to receive one or more of the implantable collagen membrane, hollow needle or cell strainer, wherein the predefined storage locations are depressions integrally formed in a surface of an inner region of the container;
   wherein the container is hermetically sealed to define an internal region in which the predefined storage locations, receptacle, hollow needle, cell strainer and implantable collagen membrane are located.

2. The kit of claim 1, wherein the container further comprises a syringe.

3. The kit of claim 2, wherein the hollow needle and syringe are provided as separate components in the container and are demountably attachable to each other.

4. The kit of claim 2, wherein the hollow needle further comprises a conduit demountably attachable at one end to the hollow needle and at an opposite end to the syringe.

5. The kit of claim 2, wherein the hollow needle is a puncture needle capable of extracting bone marrow from a patient.

6. The kit of claim 1, wherein the hollow needle is capable of aspirating the bone marrow from the patient.

7. The kit of claim 1, wherein the bone marrow to be extracted by the hollow needle is of a type that: (a) does not have a particular kind of organised structure; or (b) has an in-vivo fluid or gelatinous state.

8. A method of manufacturing an implantable medical material suitable for at least assisting in ameliorating tissue damage in a mammalian body, the method comprising: opening the kit in accordance with claim 1; placing the implantable collagen membrane in the receptacle; covering the receptacle with the cell strainer; depositing biological material collected from the mammalian body on the cell strainer and allowing autologous cells from the biological material to pass through the cell strainer onto the implantable collagen membrane;
   holding the implantable collagen membrane and autologous cells in the receptacle for a period of time to transform the implantable collagen membrane into the implantable medical material; and
   removing the implantable medical material and autologous cells from the receptacle.

9. A method of using the kit according to claim 1, the method comprising:
   opening the kit;
   placing the implantable collagen membrane in the receptacle;
   covering the receptacle with the cell strainer;
   depositing biological material collected from a mammalian body on the cell strainer and allowing autologous cells from the biological material to pass through the cell strainer onto the implantable collagen membrane;
   holding the implantable collagen membrane and autologous cells in the receptacle for a period of time; and
   removing the implantable collagen membrane and autologous cells from the receptacle.

10. The method of claim 8, wherein the period of time is between 15 minutes and 2 hours.

11. The method of claim 8, wherein the biological material is of a type that: (a) does not have a particular kind of organised structure; or (b) has an in-vivo fluid or gelatinous state.

12. The method of claim 8, further comprising using the extractor to extract the biological material from the mammalian body prior to depositing the biological material.

13. The method of claim 9, wherein the period of time is between 15 minutes and 2 hours.

* * * * *